United States Patent [19]

Alliger

[11] Patent Number: 5,248,296

[45] Date of Patent: Sep. 28, 1993

[54] ULTRASONIC DEVICE HAVING WIRE SHEATH

[75] Inventor: Howard M. Alliger, Melville, N.Y.

[73] Assignee: Sonic Needle Corporation, Farmingdale, N.Y.

[21] Appl. No.: 632,679

[22] Filed: Dec. 24, 1990

[51] Int. Cl.⁵ .................................. A61B 17/20
[52] U.S. Cl. .................. 609/22; 128/24 AA; 606/169
[58] Field of Search ............ 128/24 AA; 604/22; 606/128, 159, 169

[56] References Cited

U.S. PATENT DOCUMENTS

| | | | |
|---|---|---|---|
| 3,352,303 | 11/1967 | Delaney | 604/22 |
| 3,861,391 | 1/1975 | Antonevich et al. | 128/24 AA |
| 4,223,676 | 9/1980 | Wuchinich et al. | 604/22 |
| 4,431,006 | 2/1984 | Trimmer et al. | 128/24 AA |
| 4,474,180 | 10/1984 | Angulo | 128/24 AA |
| 4,735,604 | 4/1988 | Watmough et al. | 604/22 |
| 4,920,954 | 5/1990 | Alliger et al. | 128/24 AA |
| 5,069,664 | 12/1991 | Guess et al. | 604/22 |
| 5,116,343 | 5/1992 | Ams et al. | 604/22 |

Primary Examiner—C. Fred Rosenbaum
Assistant Examiner—Michael Rafa
Attorney, Agent, or Firm—Howard Paul Terry

[57] ABSTRACT

An ultrasonic device having a wire sheath for use in removing plaque from a human artery. This ultrasonic device has a wire for removing the plaque, a sheath around the wire for minimizing transverse displacement during cavitation; a handpiece having a portion joined to the wire at one end, and a transducer in the handpiece for vibrating the wire axially. It may also have a pips fitting having an opening for a syringe for fluid under pressure for a passageway between the wire and sheath.

9 Claims, 2 Drawing Sheets

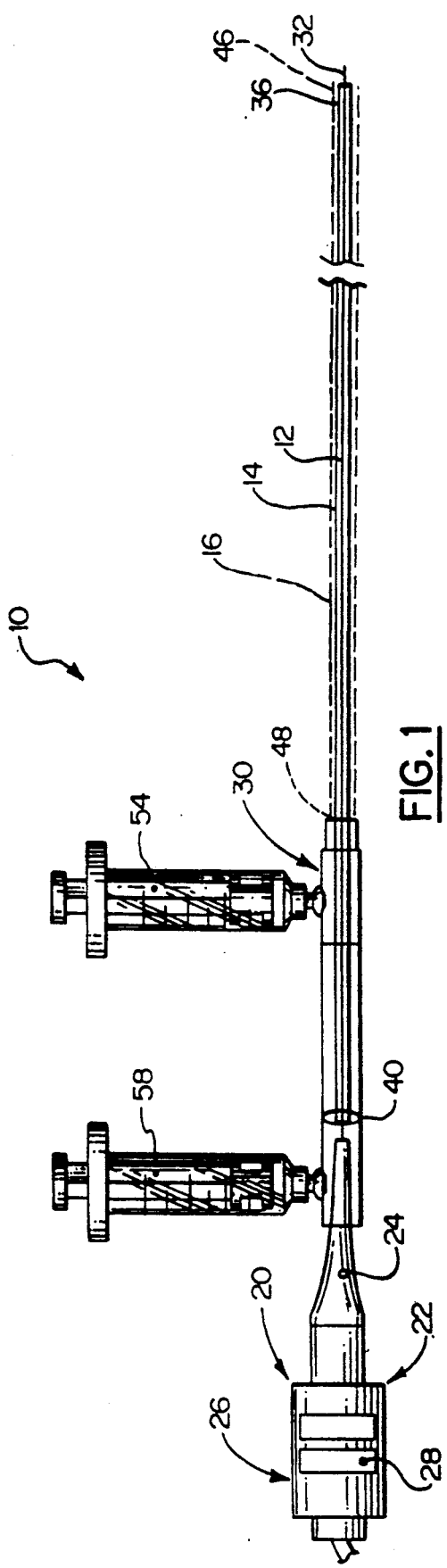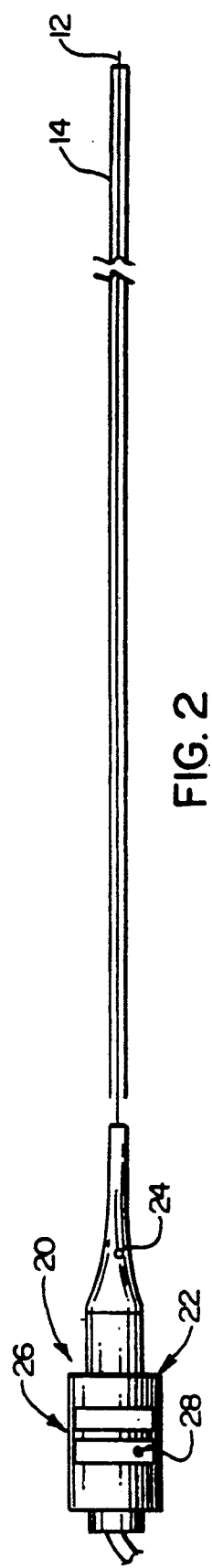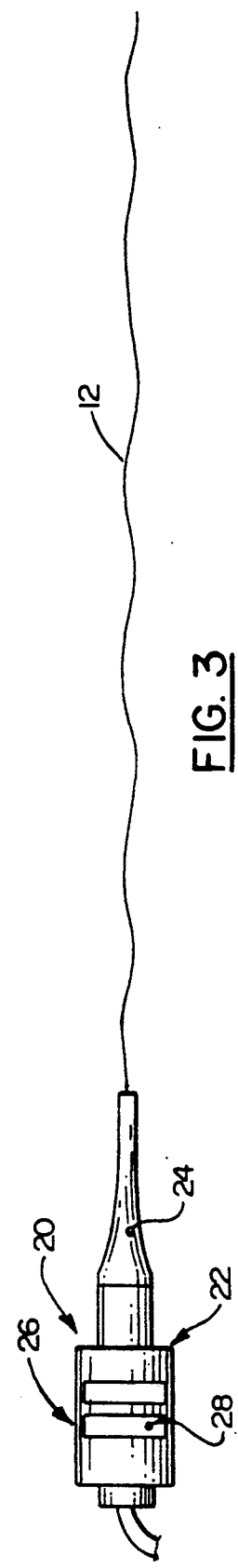

ULTRASONIC DEVICE HAVING WIRE SHEATH

The invention generally relates to an ultrasonic device having a wire sheath, and in particular the invention relates to an ultrasonic device having a wire which acts as an ultrasonic waveguide and having a closely fitting wire sheath disposed around the wire to minimize undesirable transverse motion of the wire.

BACKGROUND OF INVENTION

The prior art ultrasonic device for applying cavitation force to plaque in a human artery is described in U.S. Pat. No. 4,920,954, which is assigned to the same assignee as this application. Related prior art patents and publications are described in such prior art U.S. Pat. No. 4,920,954. Another related prior art patent is U.S. Pat. No. 4,870,953.

Ultrasound devices have become means of disintegrating and removing tissue within the human body. For example, the phacoemulsifier for removing cataracts, the ultrasonic surgical aspirator for removing tumors, the ultrasonic kidney stone breaker, the ultrasonic prosthesis remover, the ultrasonic atheroma remover for blood vessels, and the ultrasonic wire to eliminate arrhythmia.

It is highly desirable for such a device to deliver ultrasonic energy percutaneously, from outside the body, to the tissue in question by means of a long wire. So doing avoids an open field operation. However, one of the problems involved with directing sonic energy down the length of a wire is that of unwanted transverse or perpendicular motion of the wire. When the wire vibrates transversely instead of axially, the tip amplitude, or forward-and-back motion, is diminished or eliminated so that the production of cavitation, i.e., the making and breaking of bubbles, is diminished as well. Since the purpose of the ultrasonic wave guide is to establish cavitation at the distal end, the usefulness of the sonic energy transfer is reduced as the wire gets more flexible and side-to-side motion increases.

In order to reach the kidney from the urethra, for example, to break a kidney stone, or to reach the coronary arteries from the groin to disintegrate an arterial occlusion, a very thin wire is necessary since the blood vessel or duct is usually sinuous. The wire must be flexible enough so that the artery or ureter or other duct will not be injured or straightened. Also it must be thin and flexible to avoid bending stresses within the wire itself which would cause heating by absorbing the moving sound wave.

In the past, when ultrasonic wires are inserted into the body, they are generally accompanied by a surrounding catheter. The catheter has several functions: to protect the artery or duct from puncture as the wire is inserted, to cool the wire which might otherwise got red hot, to irrigate the distal sonicated tissue or stone, or to aspirate the disintegrated debris. When the ultrasonic wire is used in blood vessel work, the catheter is sometimes used to infuse heparin, saline, contrast medium, or streptokinase during the procedure for their chemical effect in the artery. The inside diameter and thickness of the catheter is not important to the proper operation of the wire and was not previously described in the patent or scientific literature. If the catheter were made smaller in diameter, it could not perform the functions for which it was designed, such as removing debris, or infusing heparin. Similarly, the plastic material of which the catheter is made was also not important in the past to the users of the ultrasonic wire.

The catheters used in the past with ultrasonic wires did not prevent transverse motion in any way. In fact, U.S. Pat. No. 4,870,953 by Robert J. Siegel, taught that it was necessary to maximize transverse motion in an ultrasonic waveguide for disruption of arterial occlusions. The only mention of the prevention of transverse motion in the patent literature is made in U.S. Pat. No. 4,920,954. Here, this motion is minimized by the type of wire used, the type of horn energizing the wire, and the electronic control feeding the system.

One problem with the prior art ultrasonic device is that as the wire is made thinner, or of a more flexible metal such as titanium or aluminium, the wire when energized by sound pulses from one end, tends to whip sideways, sinusoidally, and the wire tip can be seen to stop its axial motion. The unwanted side-to-side motion is also dangerous, since it tends to break the wire, usually at the point of connection to the sound source.

SUMMARY OF THE INVENTION

According to the present invention, an ultrasonic device is provided. This device includes, a wire having a first end portion and having a second end portion for use in removing unwanted material in a normally inaccessible area by cavitation, a closely fitting sheath surrounding the wire and forming a sheath passageway therebetween and having a first end portion and having a second end portion for use in minimizing transverse displacement of the wire, support means having a handpiece having a horn end portion fixedly connected to the wire first end portion, drive means having a transducer supported by the hand piece for providing ultrasonic vibration through the horn end portion to the wire first end portion, a catheter tube surrounding the sheath and forming a catheter passageway therebetween and having a first end portion and a second end portion for threading the wire and sleeve to a position adjacent to the unwanted material, a connector subassembly having a catheter fitting having a cavity and having a peripheral wall fixedly connected to the catheter tube first end portion, and said connector subassembly having a sheath fitting having a chamber and having a peripheral wall having a seal means in sealing engagement with the shot first end portion.

By using a closely fitting sheath surrounding the wire the transverse displacement during vibration of the wire is significantly reduced. By forming a narrow passageway between the sheath and the wire and introducing a fluid therein, the underside transverse motion of the wire is further decreased.

In certain procedures, a catheter is not necessary or advisable. This is the case where material does not have to be injected or withdrawn, or when the artery, vessel or duct is particularly narrow and cannot accommodate the surrounding catheter.

The foregoing and other objects, features and advantages will be apparent from the following description of the preferred embodiment of the invention as illustrated in the accompanying drawings.

BRIEF DESCRIPTION OF THE DRAWINGS

FIG. 1 is an elevation view of an ultrasonic device according to the invention;

FIG. 2 is an elevation view of a portion of FIG. 1;

FIG. 3 is a schematic view of the portion of FIG. 2 during vibration with its sheath removed;

DESCRIPTION OF THE PREFERRED EMBODIMENT

Figures 4, 5:
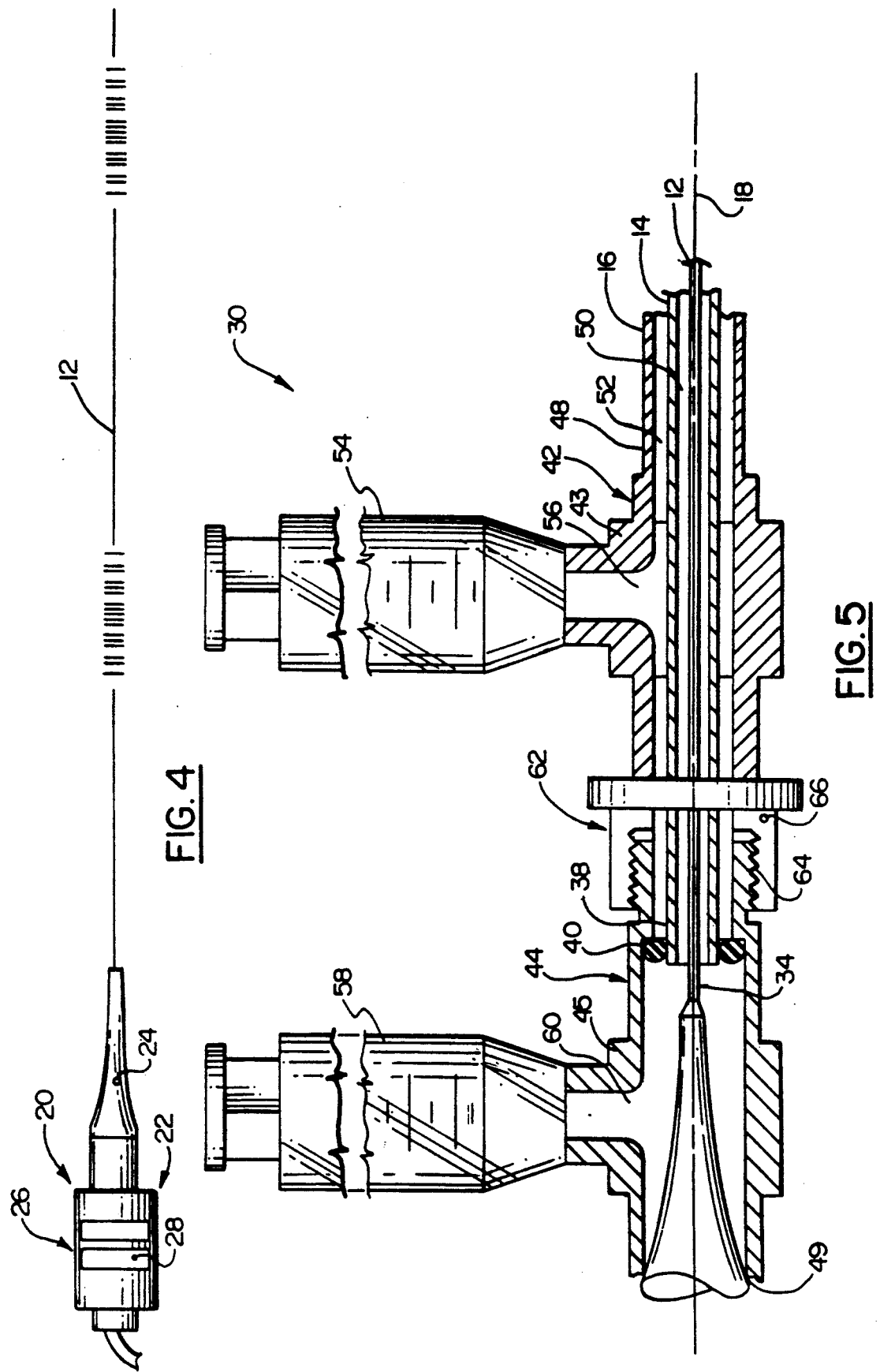
FIG. 4 is a schematic view of the portion of FIG. 2 during vibration with its sheath in place.
FIG. 5 is an enlarged view of a portion of FIG. 1.

As shown in FIGS. 1 through 5, an ultrasonic device 10 is provided, Device 10 has a wire 12, a close fitting sheath or sleeve 14, and may also have a catheter tube 16, all of which are coaxial along axis 18. Device 10 also has a support means 20, which has a handpiece 22, connected to a horn portion 24. The horn portion 24 may be tapered as more fully explained in U.S. Pat. No. 4,920,954. Device 10 also has a drive means 26, comprising a transducer or converter or piezoelectric crystal unit 28. Device 10 aim has a to catheter and sheath connecting subassembly or connector 30.

As shown in FIGS. 1 and 5, wire 12 has an axially outer end 32, and has an axially inner end 34, which is fixedly connected to horn portion 24. Sheath 14 has an outer end 36, and has an inner end 38 which has a seal ring 40 that engages connector 30.

Connector 30 has a catheter fitting 42, which has a peripheral wall 43. Connector 30 also has a sheath fitting 44, which has a peripheral wall 45 that seatingly engages tapered horn portion 24 at 49. Catheter tube 16 has an outer end 46, and has an inner end 49 which is fixedly connected to catheter fitting peripheral wall 43 by a luer lock or similar fitting.

As shown in FIG. 3, sheath 14 has a sheath passageway 50 between its inner diameter surface and an outer diameter surface of wire 12. Catheter tube 16 has a catheter passageway 52 between its inner diameter surface and an outer diameter surface of sheath 14.

Catheter fitting 42 has a contrast fluid syringe 54, which is a cylinder and piston type of syringe. Catheter fitting 42 also has a cavity 56, which connects to catheter passageway 52. Sheath fitting 44 has a pressurizing viscous fluid syringe 58, which is a cylinder and piston type of syringe. Sheath fitting 44 also has a chamber 60, which connects to sheath passageway 50.

Fittings 42, 44 have an adjustable coupling unit 62, which is disposed therebetween. Coupling unit 62 is similar to a garden hose type of coupling unit. Coupling unit 62 has a fixed portion 64, which is fixedly connected to peripheral wall 43, and has a rotatable portion 66, which can rotate relative to fixed portion 64, for axially projecting wire outer end 32 beyond catheter tube outer end 46 when causing cavitation, and for axially retracting wire outer end within catheter tube outer end 46 when threading wire 12 to the desired location in an artery, or the like.

Device 10 minimizes transverse or perpendicular motion in wire 12, even with very thin diameter wires and flexible alloys. Sheath 14 is preferably thin, flexible, and slippery. Sheath 14 is as close fitting as possible but not tight enough to prevent the needed longitudinal motion of the wire. A minimum radial separation of 0.003" is between wire and sheath, or a difference in diameter of 0.006" between the i.d. of the sheath and the o.d. of the wire, and preferably the radial separation is not much more than 0.006", or an 0.012" total difference in diameters. The shivering motion of the wire 12 is then highly restricted and, importantly, without reducing cavitation at the open vibrating tip. Sheath 14 is a tubing with a wall thickness of about 0.006". Making sheath 14 much thicker than this reduces flexibility, and much thinner causes the sheath to bunch up, or form accordion pleats, as the wire is inserted or pulled back and forth through the surrounding catheter. Sheath 14 can be a tube made of plastic, sold under the trademark "TEFLON".

Sheath passageway 50 may have a liquid which decreases transverse movement further and only slightly increases the viscous drag on the axial motion of the wire. Without the close filling sheath, however, the lateral damping effect of the liquid is not noticeable.

The liquid in sheath passageway 50 is preferably a viscous fluid, such as contrast medium, plasma, sodium hyaluronate, or dextran although saline can be used.

Pressure is applied on the liquid in sheath passageway 50 fluid in order to damp out virtually all transverse motion. This can, for example, be applied by hand with a syringe or pump 58. Since the space between sheath and wire is relatively small, very little fluid flows out the end in the short "on-time" of the ultrasound, even with the added liquid pressure. Pressures range up to 150 psi depending upon the viscosity of the fluid and the diameter of the wire.

The advantages of device 10 are indicated hereafter.

With device 10, the smallest, most flexible wires, 5 feet long, can be used with ultrasound to apply cavitation force at a distal site within the body. For example a 0.017" titanium wire (0.43 mm) can now be threaded to a stone within the kidney, a gallstone within the gallbladder, or an occlusion in an artery near the ankle or in the heart, while avoiding the danger of puncture and dissection.

Further, the power loss down the wire is minimized by this invention in several ways, For one, since the wire can now be made thin, there is less tension and compression within the wire mass as it is bent. The strains of tension and compression break up the sound wavefront and also change the speed of sound in the wire. The wavelength of the sound wave now doesn't match the natural resonant frequency of the tuned wire and causes heat loss. Two, heat loss due to lateral vibration and shivering of the wire is now avoided. With all the losses, combined, without cooling liquid, the temperature of the wire can quickly rise above boiling with power inputs necessary to disintegrate tissue.

Device 10 reduces the overall power loss. Viscous fluid within the sheath, together with high pressure in the fluid, eliminates cavitation at the flat tip feeding the wire, and this reduces heat as well as noise.

While the invention has been described in its preferred embodiment, it is to be understood that the words which have been used are words of description rather than limitation and that changes may be made within the purview of the appended claims without departing from the true scope and spirit of the invention in its broader aspects.

I claim:

1. An ultrasonic device comprising:
   a wire having a first end portion and having a second end portion for use in removing unwanted material in a normally inaccessible area by cavitation;
   a close fitting sheath surrounding the wire along the majority of the length of the wire for dampening transverse displacement of the wire in the proximity of the sheath;
   said sheath and wire forming a sheath passageway therebetween;
   support means having a handpiece having a horn end portion fixedly connected to the wire first end portion; and drive means having a transducer supported by the handpiece for providing ultrasonic vibration through the horn end portion to the wire first end portion;

wherein the sheath has an inside diameter and the wire has an outside diameter and the difference between the sheath inside diameter and the wire outside diameter is in the range of about 0.006 inches to 0.012 inches.

2. An ultrasonic device comprising:

a wire having a first end portion and having a second end portion for use in removing unwanted material in a normally inaccessible are a by cavitation;

a close fitting sheath surrounding the wire along the majority of the length of the wire for dampening transverse displacement of the wire in the proximity of the sheath;

said sheath and wire forming a sheath passageway therebetween;

support means having a handpiece having a horn end portion fixedly connected to the wire first end portion;

drive means having a transducer supported by the handpiece for providing ultrasonic vibration through the horn end portion to the wire first end portion;

wherein the sheath passageway contains a fluid for dampening transverse displacement of the wire; and wherein means including a fitting is provided for pressurizing the fluid for further dampening transverse displacement of the wire.

3. An ultrasonic device comprising:

a wire having a first end portion and having a second end portion and having an outside diameter.

a close fitting sheath surrounding the wire along its entire length and forming a passageway therebetween and having an inside diameter;

a handpiece having an end portion fixedly connected to the wire first end portion;

a transducer supported by the handpiece for vibrating the wire;

a fitting having a chamber connected to said passageway and adapted for pressurizing fluid in the chamber and passageway; and said wire outside diameter and said sheath inside diameter having a difference in the range of 0.006 to 0.012 inches for dampening transverse displacement of the wire.

4. An ultrasonic device comprising:

a wire having a first end portion and having a second end portion for use in removing unwanted material in a normally inaccessible area by cavitation;

a close fitting sheath surrounding the wire and forming a sheath passageway therebetween and having a first end portion and having a second end portion for use in minimizing transverse displacement of the wire;

support means having a handpiece having a horn end portion fixedly connected to the wire first end portion;

drive means having a transducer supported by the handpiece for providing ultrasonic vibration through the horn end portion to the wire first end portion;

a catheter tube surrounding the sheath and forming a catheter passageway therebetween and having a first end portion and having a second end portion for disposing the wire and sheath at a position adjacent to the unwanted material;

a connector subassembly having a catheter fitting having a cavity and having a peripheral wall fixedly connected to the catheter tube first end portion; and said connector subassembly having a sheath fitting having a chamber and having a peripheral wall and having a seal means for separating the chamber from the cavity.

5. The device of claim 4, wherein the connector subassembly has a coupling unit disposed between the catheter fitting a peripheral wall and the sheath fitting a peripheral wall, said coupling unit having a fixed portion fixedly connected to the sheath fitting peripheral wall, and said coupling unit having a rotatable portion rotatably connected to the catheter fitting peripheral wall.

6. The device of claim 4, wherein the sheath passageway contains a fluid and wherein the sheath fitting has an opening adapted to receive fluid for supply of the sheath passageway through the chamber.

7. The device of claim 6, wherein the fluid is a viscous fluid.

8. The device of claim 6, wherein means including the sheath fitting is provided for pressurizing the fluid in the chamber and sheath passageway.

9. The device of claim 6, wherein the catheter passageway contains a fluid and wherein the catheter fitting has an opening receiving a syringe containing fluid for supply of the cavity and catheter passageway.

* * * * *